United States Patent
Op Den Buijs et al.

(10) Patent No.: US 10,593,000 B2
(45) Date of Patent: Mar. 17, 2020

(54) SYSTEM AND METHOD FOR DETERMINING THRESHOLDS OR A RANGE OF VALUES USED TO ALLOCATE PATIENTS TO A TREATMENT LEVEL OF A TREATMENT PROGRAM

(71) Applicants: Jorn Op Den Buijs, Eindhoven (NL); Maartje Helena Schonenberg, Eindhoven (NL); Petrus Nicolaas Wouters, Oostelbeers (NL); Steffen Clarence Pauws, Eindhoven (NL)

(72) Inventors: Jorn Op Den Buijs, Eindhoven (NL); Maartje Helena Schonenberg, Eindhoven (NL); Petrus Nicolaas Wouters, Oostelbeers (NL); Steffen Clarence Pauws, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 928 days.

(21) Appl. No.: 13/932,059

(22) Filed: Jul. 1, 2013

(65) Prior Publication Data
US 2014/0019161 A1 Jan. 16, 2014

Related U.S. Application Data

(60) Provisional application No. 61/671,195, filed on Jul. 13, 2012.

(51) Int. Cl.
*G06Q 50/22* (2018.01)
*G06Q 30/06* (2012.01)

(52) U.S. Cl.
CPC ......... *G06Q 50/22* (2013.01); *G06Q 30/0631* (2013.01)

(58) Field of Classification Search
CPC ...... G06Q 50/22; G06Q 50/24; G06F 19/322; G06F 19/323–327

(Continued)

(56) References Cited

U.S. PATENT DOCUMENTS 6,081,786 A * 6/2000 Barry .................. G06F 19/3443
                                                                       705/2
8,200,506 B2 * 6/2012 Kil ........................ G06F 19/345
                                                                       705/2

(Continued)

FOREIGN PATENT DOCUMENTS

WO     2011097313 A1     8/2011

OTHER PUBLICATIONS

Henry A. Glick, Cost-Effectiveness Analysis, University of Pennsylvania, Apr. 19, 2012, 25 pages.*

(Continued)

*Primary Examiner* — Jason S Tiedeman

(57) ABSTRACT

A threshold value or range of values for results of a test used to assign patients to a particular level of treatment for a clinical condition is determined based on historical information on a plurality of patients having the clinical condition. The historical information may include values for the test performed on the patients, information on the treatment level for the clinical condition provided to the patients, information on the outcome of the clinical condition for the patients, and information on the cost associated with providing each of the treatment levels to the patients. The threshold value or range of values for results of the test is determined from the historical information, with the threshold value or range of values indicating the most cost effective treatment level for a given test result.

10 Claims, 6 Drawing Sheets

(58) Field of Classification Search
USPC .......................................................... 705/2, 3
See application file for complete search history.

(56) References Cited

U.S. PATENT DOCUMENTS

| | | | | |
|---|---|---|---|---|
| 2005/0182659 A1* | 8/2005 | Huttin | ..................... | G06F 19/327 |
| | | | | 705/2 |
| 2005/0216312 A1* | 9/2005 | Bellin | ..................... | G06Q 10/10 |
| | | | | 705/3 |
| 2006/0085225 A1 | 4/2006 | Gold | | |
| 2006/0129427 A1* | 6/2006 | Wennberg | .............. | G06F 19/328 |
| | | | | 705/2 |
| 2006/0289020 A1* | 12/2006 | Tabak | ..................... | G16H 50/20 |
| | | | | 128/898 |
| 2007/0033075 A1* | 2/2007 | Hoffman | ................ | G06Q 50/22 |
| | | | | 705/3 |
| 2007/0161868 A1* | 7/2007 | Root | ..................... | G01N 33/6815 |
| | | | | 600/300 |
| 2007/0179809 A1* | 8/2007 | Brown | ................... | G06Q 30/02 |
| | | | | 705/2 |
| 2008/0147440 A1* | 6/2008 | Kil | ......................... | G06F 19/345 |
| | | | | 705/2 |
| 2008/0166348 A1* | 7/2008 | Kupper | ................. | C07K 16/241 |
| | | | | 424/136.1 |
| 2009/0326976 A1* | 12/2009 | Morris | ................................ | 705/2 |
| 2010/0030574 A1* | 2/2010 | Coe | ....................... | G06F 19/325 |
| | | | | 705/2 |
| 2010/0125462 A1* | 5/2010 | Aggarwal | .............. | G06Q 50/22 |
| | | | | 705/3 |
| 2011/0082712 A1* | 4/2011 | Eberhardt, III | ..... | G06F 19/3437 |
| | | | | 705/4 |
| 2011/0119212 A1* | 5/2011 | De Bruin | ................. | A61B 5/00 |
| | | | | 706/12 |
| 2011/0282685 A1* | 11/2011 | Kauppinen | ......... | G06F 19/3481 |
| | | | | 705/3 |
| 2012/0016690 A1* | 1/2012 | Ramarajan | ............ | G06F 19/345 |
| | | | | 705/2 |
| 2012/0296660 A1* | 11/2012 | Myers | .................... | G06Q 50/22 |
| | | | | 705/2 |
| 2013/0006649 A1* | 1/2013 | Rangadass | ............. | G06Q 10/00 |
| | | | | 705/2 |
| 2014/0314765 A1* | 10/2014 | DePinho | ............ | G01N 33/5011 |
| | | | | 424/138.1 |

OTHER PUBLICATIONS

Sonnenberg et al., Markov Models in Medical Decision Making: A Practical Guide, SAGE Publications, vol. 13, No. 4, Oct.-Dec. 1993, pp. 322-338.*

T.A. McDonagh et al., "NTproBNP and the Diagnosis of Heart Failure: A Pooled Analysis of Three European Epidemiological Studies", European Journal of Heart Failure, 6 (2004), pp. 269-273.

* cited by examiner

| Patient ID | Date of birth | Date of enrolment | NTproBNP level | CDM program level | Hospital admission dates | Date of death |
|---|---|---|---|---|---|---|
| 65 | 23-01-1964 | 17-01-2001 | 1339 | I | N/A | 13-05-2001 |
| 68 | 14-06-1955 | 18-04-2003 | 542 | I | N/A | N/A |
| 70 | 18-03-1967 | 02-05-2002 | 12237 | II | 19-07-2002 | 15-09-2002 |
| 76 | 18-12-1943 | 19-07-2002 | 5517 | II | 25-07-2002, 14-12-2002, 19-01-2003 | N/A |

FIG. 2

| Variable | Value |
|---|---|
| Cost of program level I | EUR 5000 / year |
| Cost of program level II | EUR 10000 / year |
| Cost of hospitalization | EUR 5000 |
| Time span of interest | 5 years |
| Willingness to pay | EUR 50,000 for one quality-adjusted life year |
| Discount rate cost | 4% / year |
| Discount rate effect | 1.5% / year |

Patient details

| | |
|---|---|
| Patient Name : | McBride, Erica M. |
| Age : | 65 |
| Gender : | ○ Male |
| | ⊙ Female |
| BMI : | 31 kg/m² |
| Blood pressure : | 132 over 84 mmHg |
| NTproBNP : | 2000 pg/ml |
| Urea : | 8.7 mmol/l |
| Quality of life : | Good ▼ |

[Save] Saved data for McBride, Erica M. on: 9:40:06 20 Mar 2012

▶ Clinical settings

▶ Cost settings

▶ Recommendation details

Recommendation

For this patient, the most cost-effective strategy is Motiva Guide

[Bar chart with y-axis 0.0, 1.7, 3.3, 5.0 and x-axis categories: Usual Care, Motiva Guide, Motiva Coach, Motiva Monitor]

▨ Net health benifits (QALY)
▩ Annual hospital costs (kEUR/yr)

FIG. 10

SYSTEM AND METHOD FOR DETERMINING THRESHOLDS OR A RANGE OF VALUES USED TO ALLOCATE PATIENTS TO A TREATMENT LEVEL OF A TREATMENT PROGRAM

TECHNICAL FIELD OF THE INVENTION

The invention relates to treatment programs for chronic diseases that have a number of different intensity levels of treatment available to a patient, and in particular relates to a system and method for determining threshold values or a range of values for a test used to assess the current condition of the patient, the threshold values or range of values being used to allocate patients to an appropriate intensity level of treatment for the current status of the disease for the patient.

BACKGROUND TO THE INVENTION

With the average age of the population increasing, the number of people with chronic diseases is also increasing. There is a lack of healthcare staff that are able to manage patients with chronic diseases and costs of treatments are rising, which has stimulated interest in developing chronic disease management (CDM) programs to try and avoid costly hospital readmissions. One example of a CDM program is home telemonitoring of patients with heart failure.

Disease management programs can follow a 'tiered' approach, with each tier or level of service corresponding to a particular "intensity" of monitoring, clinical attention and/or intervention, with the tier or level allocated being selected based on the severity level of the disease and, perhaps, the personal preferences of the patient. Depending on the medical condition, the different tiers can comprise different amounts or doses of a particular medication, different types of medication, different hospital- or home-administered tests and/or different (or some) surgical interventions. Generally, the more 'intense' the tier of service in the disease management program, the higher the financial cost of providing that service. As a result, certain programs or tiers of service may only become cost-effective at a certain level of disease severity.

A system and method for performing a cost-utility analysis of pharmaceutical interventions has been previously described in US 2007/0179809 A1. In this system, a patient perceived value, a utility value, an objective value and clinical trial data for various pharmaceutical interventions is compared to derive a gain per dollar expended for each pharmaceutical intervention, so that the most effective pharmaceutical intervention for the money expended can be chosen.

For some chronic diseases, the severity level of the disease can be objectively quantified using a test pertaining to the chronic disease performed in a laboratory or by equipment the patient can have at home. For example, N-terminal prohormone brain natriuretic peptide (NT-proBNP) levels are a quantitative measure of the acuity level in heart failure patients ("NTproBNP and the diagnosis of heart failure: a pooled analysis of three European epidemiological studies", European Journal of Heart Failure, 6 (2004), 269-273 by McDonagh, T. A., Holmer, S., Raymond, I., Luchner, A., Hilderbrant, P. and Dargie, H. J.). The test for the NTproBNP level is generally performed in a laboratory or in a clinical setting to determine the prognosis for the patient.

SUMMARY OF THE INVENTION

It is an object of the current invention to be able to use the values obtained using these laboratory, clinical or home tests to aid the patient and/or responsible care giver to select an appropriate intensity level of a disease management or treatment program, once the disease has been diagnosed by a qualified physician.

It is another object of the invention to provide a system and method that can determine cut-off or threshold values for the test or tests which can be used to indicate the tier of service of the disease management or treatment program that is most cost-effective for the patient.

According to a first aspect of the invention, there is provided a system for determining a threshold value or range of values for results of a test used to assign patients to a particular level of treatment for a clinical condition, the system comprising one or more databases storing historical information on a plurality of patients having the clinical condition, the information including values for the test performed on the patients, information on the treatment level for the clinical condition provided to the patients, there being a plurality of available treatment levels for the clinical condition, information on the outcome of the clinical condition for the patients and information on the cost associated with providing each of the treatment levels to the patients; and a processing module in communication with said one or more databases, the processing module determining a threshold value or range of values for results of the test from the information in said one or more databases, with the threshold value or range of values indicating the most cost effective treatment level for a given test result.

In some embodiments, the processing module is configured to determine a threshold value or range of values for results of the test from the information by determining a relationship between values for the test and the health outcome of the clinical condition for each treatment level. The processing module can be configured to determine the relationship through statistical analysis of the information stored in the one or more databases.

In some embodiments, the processing module is configured to determine a threshold value or range of values for results of the test from the information by determining a relationship between values for the test and the monetary cost outcome for each treatment level. The processing module can be configured to determine the relationship through statistical analysis of the information stored in the one or more databases.

In some embodiments, the processing module is configured to determine a threshold value or range of values for results of the test from the information by determining a relationship between net health benefits and threshold values or ranges of values. The net health benefits are preferably the accumulated effect of said treatment level over a predefined time period minus the total accumulated monetary cost divided by willingness to pay, the willingness to pay being the monetary equivalent to a quality-adjusted life year.

The processing module can be configured to determine the relationship between net health benefits and threshold values or ranges of values by solving a cost-effectiveness model for each treatment level to determine net health benefits for the plurality of patients. In some embodiments, the cost-effectiveness model comprises a Markov model, differential equations or difference equations.

In some embodiments, the processing module is further configured to determine a threshold value or range of values for results of the test from the information by determining the threshold value or range of values that maximize the net health benefits; and setting the threshold value or range of values as the threshold value or range of values that maximize the net health benefits.

The processing module can be configured to determine a plurality of estimates of the threshold value or range of values and to solve the cost effectiveness model for each of the plurality of estimates.

Furthermore, the processing module can be configured to determine a threshold value or range of values for results of the test from the information by determining a relationship between values for the test and the amount of patients having values for the test at or below that value.

The processing module can additionally be configured to determine a threshold value or range of values for results of the test for respective groups of patients in the plurality of patients, wherein the respective groups of patients differ from each other in one or more of age, gender, clinical condition, hospital and geographical area.

In some embodiments, the processing module can be further configured to receive a result for the test for a patient, compare the result of the test to the determined threshold value or range of values, and to output a recommended treatment level for the patient based on the result of the comparison.

According to a second aspect of the invention, there is provided a method of determining a threshold value or range of values for results of a test used to assign patients to a particular level of treatment for a clinical condition, the method comprising obtaining historical information on a plurality of patients having the clinical condition, the information including values for the test performed on the patients, information on the treatment level for the clinical condition provided to the patients, there being a plurality of available treatment levels for the clinical condition, and information on the outcome of the clinical condition for the patients; obtaining information on the cost associated with providing each of the treatment levels to the patients; processing the information to determine a threshold value or range of values for results of the test, the threshold value or range of values indicating the most cost effective treatment level for a given test result.

In some embodiments, the step of processing the information to determine a threshold value or range of values for results of the test comprises determining a relationship between values for the test and the health outcome of the clinical condition for each treatment level. Preferably, the step of determining the relationship comprises statistically analyzing the obtained information.

In some embodiments, the step of processing the information to determine a threshold value or range of values for results of the test comprises determining a relationship between values for the test and the monetary cost outcome for each treatment level. Preferably, the step of determining the relationship comprises statistically analyzing the obtained information.

In some embodiments, the step of processing the information to determine a threshold value or range of values for results of the test comprises determining a relationship between net health benefits and threshold values or ranges of values. Preferably, the net health benefits are the accumulated effect of said treatment level over a predefined time period minus the total accumulated monetary cost divided by willingness to pay, the willingness to pay being the monetary equivalent to a quality-adjusted life year.

The step of processing the information to determine the relationship between net health benefits and threshold values or ranges of values can comprise solving a cost-effectiveness model for each treatment level to determine net health benefits for the plurality of patients. Preferably, the cost-effectiveness model comprises a Markov model, differential equations or difference equations.

In some embodiments, the step of processing the information to determine a threshold value or range of values for results of the test further comprises determining the threshold value or range of values that maximize the net health benefits; and setting the threshold value or range of values as the threshold value or range of values that maximize the net health benefits.

The method can further comprise the step of determining a plurality of estimates of the threshold value or range of values, and wherein the step of processing can comprise solving the cost effectiveness model for each of the plurality of estimates.

In some embodiments, the step of processing the information to determine a threshold value or range of values for results of the test comprises determining a relationship between values for the test and the amount of patients having values for the test at or below that value.

Furthermore, the step of processing the information can comprise determining a threshold value or range of values for results of the test for respective groups of patients in the plurality of patients, wherein the respective groups of patients differ from each other in one or more of age, gender, clinical condition, hospital and geographical area.

In further embodiments, the method further comprises the steps of receiving a result for the test for a patient; comparing the result of the test to the determined threshold value or range of values; and outputting a recommended treatment level for the patient based on the result of the step of comparing.

BRIEF DESCRIPTION OF THE DRAWINGS

For a better understanding of the invention, and to show more clearly how it may be carried into effect, reference will now be made, by way of example only, to the accompanying drawings, in which:

FIG. 2 is a table illustrating exemplary information that can be stored in the patient information database;

FIG. 3 is a table illustrating exemplary cost information that can be stored in the intervention/treatment database;

FIG. 10 is a screenshot of an application providing a recommendation for a treatment level according to the invention.

DETAILED DESCRIPTION OF THE PREFERRED EMBODIMENTS

Figure 1:
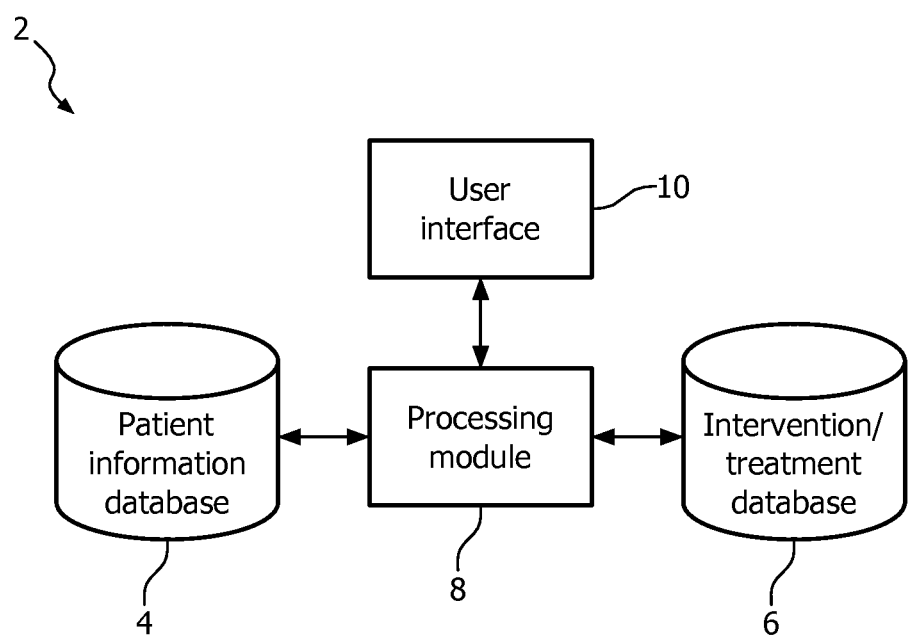
FIG. 1 is a block diagram of a system according to an embodiment of the invention.

As indicated above, it is an object of the invention to provide a system and method that can determine cut-off or threshold values for the test or tests which can be used to indicate the tier of service of the disease management or treatment program that is most cost-effective for the patient. The problem is how to determine the cut-off or threshold value of the test result at which one particular intensity treatment level of a chronic disease management program becomes more cost-effective than another one.

The most appropriate cut-off or threshold values are likely to vary by hospital/region/country due to a number of factors, including, but not limited to, variations in the range of chronic disease management (CDM) programs available and the different levels of intensity of the treatment offered; variations in the effect of the treatment level on patient survival and use of care resources; variations in patient case-mix, age and gender; variations in the perceived quality of life for different severity levels of the disease or condition; variations in the amount of money that society is willing to pay for one (quality-adjusted) life year gained by the treatment level; variations in patient motivational aspects, including knowledge of the disease, and personal preferences for intensity of the treatment administered as part of the chronic disease management program; and variations in patient ability to adhere to the prescribed program level.

A treatment program provides care to individuals diagnosed with a certain disease, such as heart failure, diabetes, cancer, or kidney failure, and who are in need of treatment. A telemonitoring program for heart failure patients is an example of a treatment program where the levels of service can follow a tiered approach. In such a telemonitoring program, one tier for patients at highest risk could comprise the combination of vital sign monitoring, tailored coaching and education, as well as weekly telephone contact with a heart failure nurse. Another level for patients at medium risk would comprise coaching and education and weekly nurse telephone contact, but not include daily weight and blood pressure measurements. Finally, a tier for patients at low risk would comprise only weekly telephone support.

An exemplary system for determining cut-off or threshold values according to the invention is shown in FIG. 2. The system 2 comprises a patient information database 4 that stores or holds information on patients, such as patient health records, that indicates details of the patient, such as any of age, gender, ethnicity, current/previous medical conditions, test results obtained using home, clinical or laboratory tests, the treatment program used to treat the medical condition(s) (including the intensity levels of the treatment program used) and/or the outcome of the treatment program or the particular level of treatment administered (e.g. patient recovery, patient survival time, whether hospitalization was required, etc.). The information stored in the patient information database 4 may be hospital specific (i.e. only relates to patients of a specific hospital or health care provider) and/or medical condition specific (i.e. only relating to patients with one or more specified medical conditions).

Exemplary information that can be stored in the patient information database 4 is shown in FIG. 2. Thus, in this example, the patient information database 4 stores information on patients with chronic heart failure, and the information for each patient includes their date of birth, date of enrollment into the chronic heart failure treatment program, the test results at the date of enrollment (in particular the NTproBNP level), the level of treatment provided to the patient (presented in terms of level I or II, with II being more intensive than level I), the dates of hospital admission and the date of death of the patient.

It will be appreciated that the information stored in the patient information database 4 will be information that is relevant to the condition or disease of the patient. Thus, where the invention is applied to, for example, patients with diabetes, information on glycated haemoglobin (HbAlc), which is a blood marker, can be stored in the patient information database 4, and for which the invention could be used to determine threshold values. Likewise, for patients with chronic kidney disease, the level of serum creatinine could be stored in the patient information database 4, and appropriate thresholds for this measurement determined using the invention.

The information held in the patient information database 4 can be obtained from an existing hospital patient information database, or, if no existing database is available for a particular medical condition (or if sufficient information for a particular condition is not available), 'default' values can be obtained and input to the database 4 from, for example, literature studies.

The system 2 also comprises an intervention/treatment program database 6 that includes information on the treatment programs available for the relevant medical conditions. The information can indicate the different levels of intensity of the treatment program that are available, the medications (including the amounts and frequency) to be administered at each level, the test(s) required to be undertaken on or by the patient, whether hospital admission is required and/or whether surgical intervention is required. The intervention/treatment program database 6 also comprises information on the cost of the patient undergoing each intensity level of the treatment program. Exemplary information for a treatment program for chronic heart failure is shown in FIG. 3. In this example, the cost information includes the cost per year of the patient undergoing the different intensity levels of treatment, the cost of any hospitalization required for the patient, the time span of interest, the willingness to pay for one quality-adjusted life year, the discount rate cost and the discount rate effect.

The 'willingness to pay' is the monetary equivalent to a quality-adjusted life year, i.e. the amount of money which a person or society is willing to pay to gain one additional life year for the patient with maximum quality of life. Regarding the discount rate cost and discount rate effect, in general, future costs and health effects should be weighted less heavily than present ones in a cost-effectiveness analysis. Discounting is a process for computing how much resource costs or health effects at some point in the future are worth today.

It will be appreciated that although the patient information database 4 and intervention/treatment database 6 are shown as separate elements of the system 2, they can be implemented as a single database or in a single database element of the system 2.

The databases 4, 6 are connected to a processing module 8 that is able to retrieve the information stored in the databases 4, 6 and perform processing on that information to determine the threshold values for the tests used to assess the prognosis or current status of the medical condition according to the invention. These thresholds can then be used by the system 2 or by a care provider (such as a physician) or the patient to select the most cost effective treatment level to be provided to the patient.

The system 2 also comprises a user interface 10 that allows a user of the system 2 (which may be the patient, a care provider and/or system administrator) to input information into the system 2 (including the information to be stored in the databases 4, 6) and to control operation of the system 2. The user interface 10 can comprise user inputs (such as a keyboard, keypad, mouse, touch screen, etc.) and a display.

In embodiments where the system 2 can provide recommendations for the most cost-effective treatment level to be provided to the patient or to assign the patient to the most cost-effective treatment level, the user interface 10 can allow the patient or care provider to input a measured value for the appropriate test. The recommendation can then be presented to the patient or care provider via the user interface 10.

Figure 4:
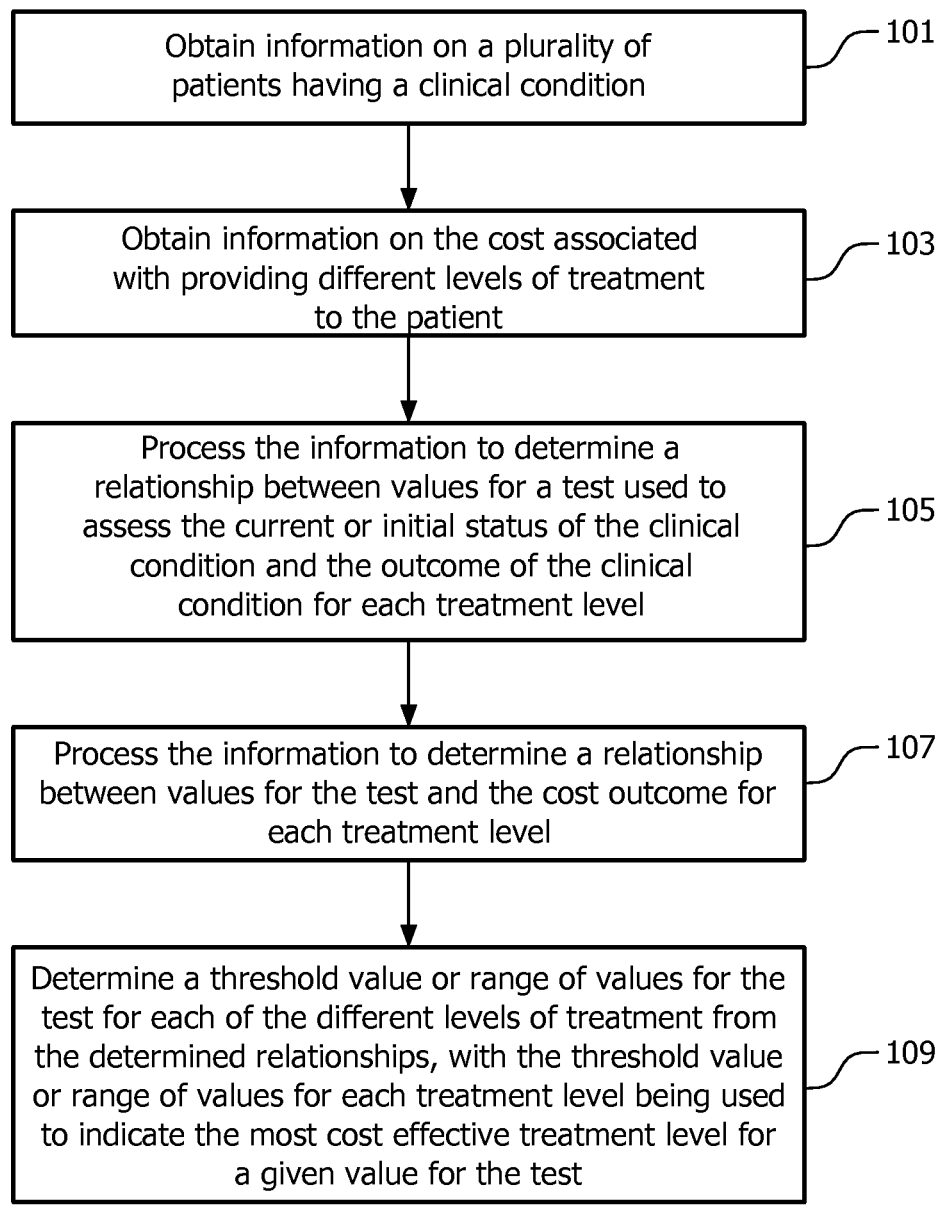
FIG. 4 is a flow chart illustrating a method according to an embodiment of the invention.

The flow chart in FIG. 4 illustrates a method of determining threshold values or a range of values for a test for use in assigning patients to the most cost-effective level of treatment for a clinical condition. The method is performed by the processing module 8. Briefly, although methods are available for performing a cost-utility analysis of pharmaceutical interventions (e.g. in US 2007/0179809), these methods do not take account of the fact that results of prognostic laboratory or home tests can be correlated with or be predictors of health effects (mortality, hospitalization and quality of life). In the case of heart failure, a patient's NTproBNP levels can be related to mortality and health care resource usage. The current invention recognizes this and uses historical patient information to derive relationships between test values and the outcome of the treatment for the patient. These relationships are then used with cost information to derive threshold values for the tests that allow the most cost effective treatment level to be selected for a patient.

In step 101, information on a plurality of patients having a particular clinical condition is obtained. The information includes values for a test (for example a home or laboratory test) performed on the patients, information on the treatment level for the clinical condition provided to the patient and information on the outcome of the clinical condition for the patient. This information is obtained by the processing module 8 from the patient information database 4.

In step 103, the processing module 8 obtains information on the cost associated with providing the different levels of treatment to the patient from the intervention/treatment database 6.

Figure 5:
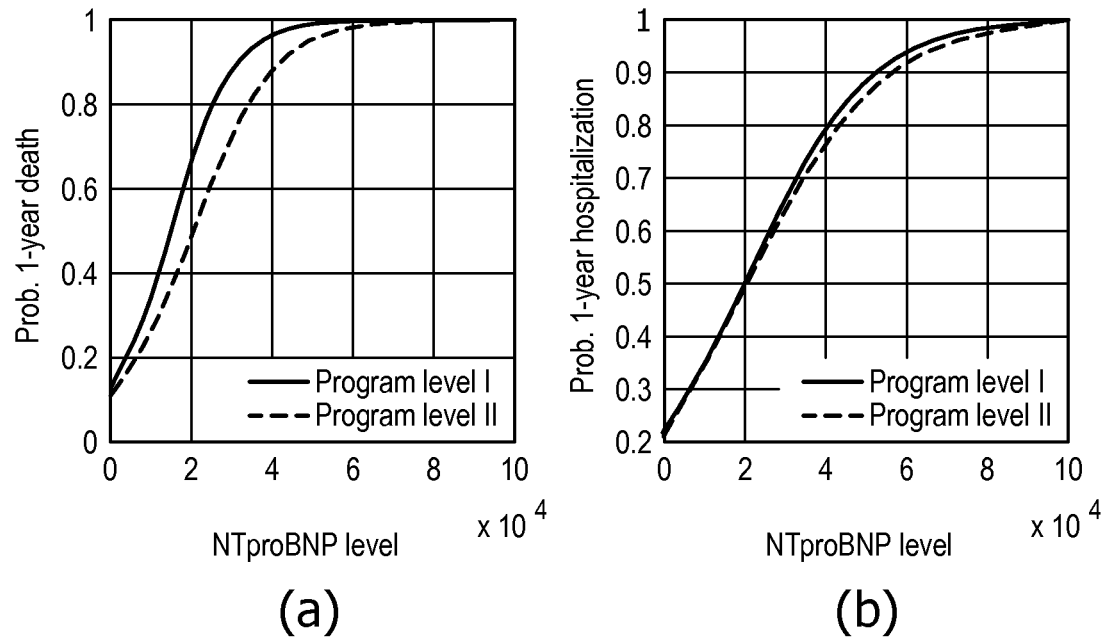
FIG. 5 illustrates exemplary relationships between test values for NTproBNP and health and financial outcomes.

Then, in step 105, the processing module 8 processes the information on the plurality of patients to determine a relationship between values for the test used to assess the current or initial status of the clinical condition and the health outcome of the clinical condition for the patient for each of the possible treatment levels of the treatment program. The outcome of the clinical condition for the patient can be measured, for example, in terms of the 1-year mortality rate, and/or the perceived quality of life. FIG. 5(*a*) shows a relationship between NTproBNP levels and health outcome (measured in terms of the probability of dying within 1 year of enrollment into the program) derived from data for patients with chronic heart failure for two different treatment levels (program level I and program level II). These relationships can be obtained from the information in the patient information database 4 by, for example, using classical statistical techniques such as linear or logistic regression of the test values on the selected outcome value. Those skilled in the art will be aware of alternative techniques that can be used to determine these relationships.

In step 107, the processing module 8 processes the information on the plurality of patients and the cost information to determine a relationship between values for the test used to assess the current or initial status of the clinical condition and the cost outcome of providing each level of treatment for the clinical condition for the patient. FIG. 5(*b*) shows a relationship between NTproBNP levels and cost outcome (measured in terms of the probability of being hospitalized within 1 year of enrollment into the program) derived from data for patients with chronic heart failure for two different treatment levels (program level I and program level II). These relationships can be obtained from the information in the patient information database 4 and information in the intervention/treatment database 6 by, for example, using linear or logistic regression of the test values on the selected cost outcome value. Again, those skilled in the art will be aware of alternative techniques that can be used to determine these relationships.

These relationships are used in step 109 to determine a threshold value or range of values for each of the different levels of treatment, with the threshold value or range of values for each treatment level being set to provide the most cost effective treatment level for a patient having a given result for the test. The threshold value or range of values for each treatment level are then output by the processing module 8 for use by a patient or health care professional in determining a level of treatment to be provided to the patient.

Briefly, in a preferred embodiment of step 109, one or more initial estimates for the cut-off or threshold value are made for each treatment level, a cost-effectiveness model (e.g., a Markov model) is simulated to establish the net health benefits of the patient population under investigation. Net health benefits are defined as the accumulated effect of the applied level of the treatment program over a given time span (measured in quality adjusted life years), from which the total accumulated costs divided by the willingness-to-pay are subtracted. A sensitivity analysis of the cut-off value can then be performed to obtain the cut-off value at which the net health benefits are maximized. Alternatively, the optimal cut-off value can be obtained by incorporating a numerical optimization algorithm within the cost-effectiveness analysis. The latter may reduce computation time if not one but multiple cut-off values are to be found (e.g. in case that there are more than two intensity levels for the chronic disease management program).

In the following paragraphs, a preferred implementation of step 109 will be described in more detail. In particular embodiments, once the relationships between test values and health outcome (step 105) and test values and cost outcome (step 107) have been derived, a relationship between test values and the fraction or percentage of patients having a test result at or below that value is also derived. This relationship can be derived by generating an (interpolated) cumulative histogram from the information in the patient information database 4, an example of which can be seen in FIG. 6.

Confounders such as age and gender can also be taken into account in the method according to the invention by determining the test threshold(s) using the approach outlined in this invention for subgroups of patients. For example, subgroups can be constructed by only considering male or female patients in the age range 40 through 60, 60 through 80 or 80 through 100, and the relationships specified in steps 105 and 107 can be derived for each subgroup. Step 109 can then be performed for each subgroup to determine the subgroup-appropriate threshold(s).

In some embodiments, thresholds for multiple types of tests can be obtained, for instance, to evaluate disease severity by assessing co-morbidities as well (for example creatinine levels for kidney failure in heart failure patients). In the case of multiple tests, multivariable relations need to be formulated. For example, the relationship between outcome and NT-proBNP and creatinine would be described by a surface instead of by a single line as is the case for NT-proBNP alone.

Figures 6, 7:
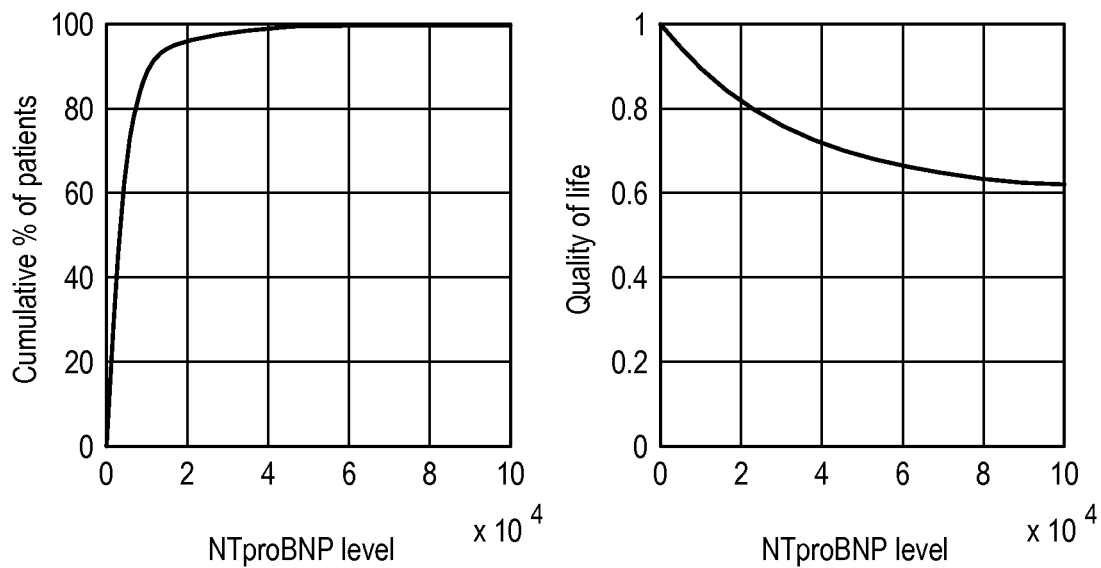
FIG. 6 is a cumulative histogram showing the number of patients having a certain test value for NTproBNP.
FIG. 7 is a graph illustrating a relationship between test values for NTproBNP and quality of life.

In an optional step, a relationship between test value and a normalized quality of life measure between 0.0 and 1.0 (e.g., perceived quality of life for patients with a certain test value) could be determined by the processing module 8 based on information from patients or informed users and/or from information in the medical literature. If such quality of life data is not provided or otherwise available, it can be assumed that all patients have the maximum quality of life equal to 1.0. An exemplary relationship between test results and quality of life is shown in FIG. 7.

Next, a cost-effectiveness model is defined. This can be in the form of a Markov model, differential equations, difference equations or another method. In the preferred embodiment described further below, the cost-effectiveness model is in the form of differential equations.

In particular, if the fraction of patients enrolled in a certain treatment program level i is $y_i$, then the rate of change of that fraction ($dy_i/dt$) depends on the average mortality rate $r_{die,i}$ among patients in program level I as follows:

$$\frac{dy_i}{dt} = -r_{die,i} y_i (i = 1, 2) \quad (1)$$

It is assumed that patients do not move from one treatment level to another, but remain within the same program level for the time span over which the future net health benefits are calculated.

The cumulative health effects E (expressed in quality adjusted life years) can then be computed as:

$$\frac{dE}{dt} = \frac{1}{(1 + r_E)^t} \sum_{i=1}^{2} q_i y_i \quad (2)$$

where $r_E$ is the discount rate for effects and $q_i$ are weights for the quality of life for patients in program level i. The cumulative costs C can be further computed from the average hospitalization costs $c_{hosp}$, the average hospitalization rate for each program level $r_{hosp,i}$ and the cost $c_{prog,i}$ for each program level i:

$$\frac{dC}{dt} = \frac{1}{(1 + r_C)^t} \sum_{i=1}^{2} (c_{hosp} r_{hosp,i} + c_{prog,i}) y_i \quad (3)$$

where $r_C$ is the discount rate for costs.

Solving the cost-effectiveness model can be achieved by solving differential equations (1), (2) and (3) by using numerical methods (e.g., Euler method or Runge-Kutta method), which are known to the skilled person. Solving the differential equations requires initial values for $y_i$ as well as a time span over which the accumulated health effects and costs are computed. Upon solving the cost-effectiveness model, the accumulated health effects E and costs C over the given time span are determined. The net health benefits (NHB) associated with the costs and effects are given by:

$$NHB = E - \frac{C}{WTP} \quad (4)$$

where E is the total health effect (in quality adjusted life years), C is the total cost, and WTP is the willingness to pay (e.g., societal willingness to pay for one quality adjusted life year).

Figure 8:
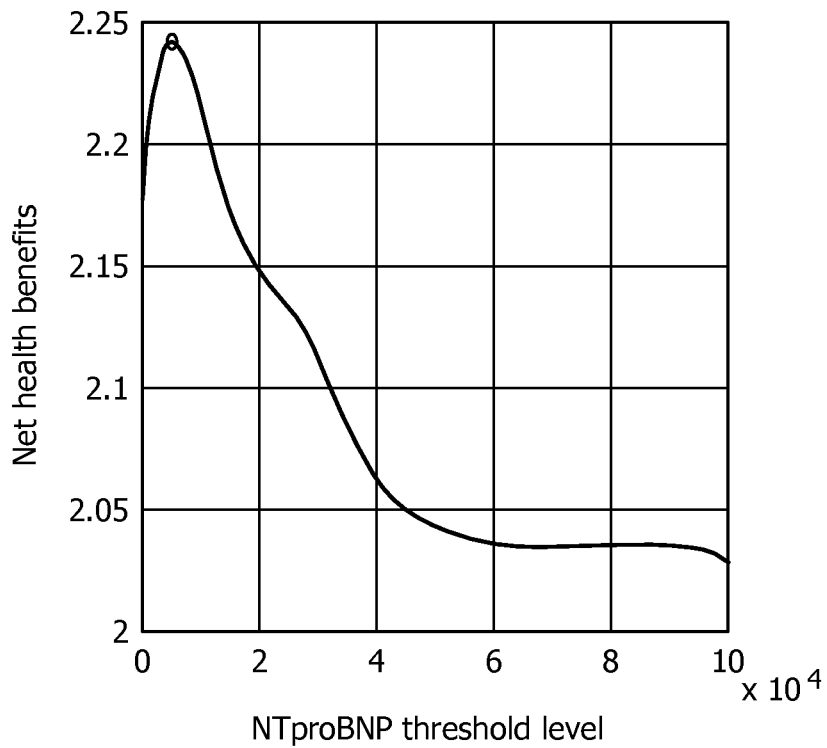
FIG. 8 is a graph illustrating the calculated net health benefits as a function of test values for NTproBNP.

The test threshold value which results in the maximum net health benefits (NHB) can then be found by simulating the cost-effectiveness model for a range of test threshold values. This is achieved by solving the differential equations (1), (2) and (3) multiple times, namely for multiple values of the test threshold. From the resulting values for the effect E and the cost C at the end of the time span, the net health benefits can then be computed using equation (4). The latter is also done for the multiple values of the test threshold. This results in a relationship between the net health benefits and the test threshold. FIG. 8 shows the net health benefits as a function of threshold values for the NTproBNP level. It is assumed that patients having a test result below the threshold of the test value will be in treatment level I and patients having a test result above the threshold will be in level II. This example only considers two treatment levels and one test threshold value.

In this example, the maximum net health benefit level was found at a NTproBNP level of 7800. This value of NTproBNP, where the maximum net health benefits are achieved, can then be set as the cut-off or threshold value above/below which patients are treated with a different treatment level.

It should be noted that the NHB are maximized here for the population under consideration (e.g., the population of typical heart failure patients that present at the hospital or area where the invention is used), not for an individual patient. To achieve maximum NHB for the patient population in the current example, all patients below the test threshold value should be enrolled in program level I, and all patients above the threshold should be enrolled in program level II.

It should be noted that the variables $r_{die,i}$, $r_{hosp,i}$, and $q_i$ as well as the initial values for solving $y_i$ ($y_{i,0}$) for each treatment level are dependent on the fraction of patients having a test value above or below the cut-off value. The initial values $y_{i,0}$ are identical to the fraction of patients within each range. The average rates are computed using the distribution of patients with a particular test result. For example, for two program levels (i=1,2) with test threshold Th, the mortality rates for the two program levels can be computed using the one-year probability of mortality $p_{die}$ as follows:

$$p_{die,1} = \frac{\int_0^{Th} p_{die}(\text{test}) N(\text{test}) d\text{test}}{\int_0^{Th} N(\text{test}) d\text{test}} \quad (5)$$

$$p_{die,2} = \frac{\int_{Th}^{\infty} p_{die}(\text{test}) N(\text{test}) d\text{test}}{\int_{Th}^{\infty} N(\text{test}) d\text{test}} \quad (6)$$

Here $p_{die}$ and the fraction of patients N with certain NTproBNP level are functions of the test value. The probability can be converted to a rate using $$r = \frac{1}{dt} \ln(1 - p) \quad (7)$$

with dt the time span of interest (e.g., one year). In a similar fashion, average hospitalization rates and quality of life for each program level can be computed.

If multiple cut-off values need to be defined (e.g., two thresholds in the case where there are three levels of intensity in the treatment program), the net health benefits can be computed as a function of the multiple threshold values in order to be able to compute the maximum net health benefits.

In the case of M treatment levels, the equations (1)-(3) and (5)-(6) above can be generalized to:

$$\frac{dy_i}{dt} = -r_{die,i} y_i (i = 1, \ldots, M) \qquad (8)$$

$$\frac{dE}{dt} = \frac{1}{(1+r_E)^t} \sum_{i=1}^{M} q_i y_i \qquad (9)$$

$$\frac{dC}{dt} = \frac{1}{(1+r_C)^t} \sum_{i=1}^{M} (c_{hosp} r_{hosp,i} + c_{prog,i}) y_i \qquad (10)$$

$$p_{die,i} = \frac{\int_{Thi-1}^{Thi} p_{die}(\text{test}) N(\text{test}) d\text{test}}{\int_{Thi-1}^{Thi} N(\text{test}) d\text{test}} \qquad (11)$$

where Thi and Thi-1 for a particular treatment level are determined according to the position of the treatment level in the hierarchy of treatment levels. For example, in the case of three treatment levels, the three versions of equation (11) will be:

$$p_{die,1} = \frac{\int_{0}^{Th1} p_{die}(\text{test}) N(\text{test}) d\text{test}}{\int_{0}^{Th1} N(\text{test}) d\text{test}} \qquad (12)$$

$$p_{die,2} = \frac{\int_{Th1}^{Th2} p_{die}(\text{test}) N(\text{test}) d\text{test}}{\int_{Th1}^{Th2} N(\text{test}) d\text{test}} \qquad (13)$$

$$p_{die,3} = \frac{\int_{Th2}^{\infty} p_{die}(\text{test}) N(\text{test}) d\text{test}}{\int_{Th2}^{\infty} N(\text{test}) d\text{test}} \qquad (14)$$

In equations (12)-(14), Th1 and Th2 are the thresholds for the transition from treatment level I to II and treatment level II to II respectively. Furthermore, in solving the differential equations and maximizing the net health benefits (NHB), it should be ensured that Th2>Th1.

Figure 9:
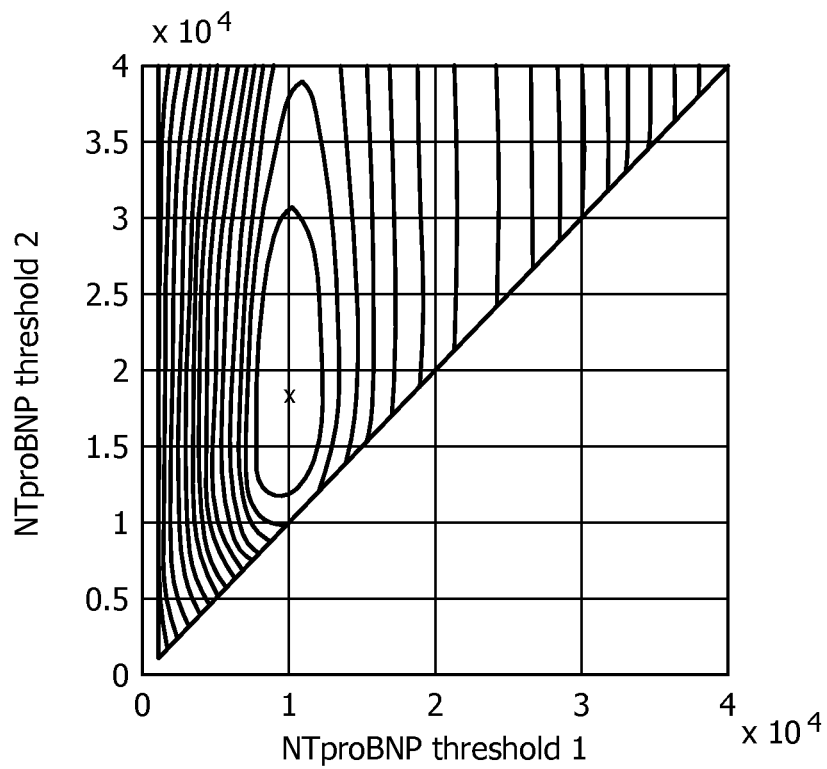
FIG. 9 is a contour plot of net health benefits as a function of two threshold values.

A contour plot showing net health benefits as a function of the two threshold values is shown in FIG. 9. It can be seen that the maximum net health benefits occur at the point marked 'x' with a value of approximately $1 \times 10^4$ for the first threshold (i.e. the threshold between levels 1 and 2) and a value of approximately $1.8 \times 10^4$ for the second threshold (i.e. the threshold between levels 2 and 3). Alternatively, an optimization algorithm can be implemented (for example a Levenberg-Marquardt algorithm) to compute the local maximum of NHB faster. In the latter case, the differential equations are solved for initial estimates of Th1 and Th2, which are then adapted in a "smart" fashion to maximize NHB and to arrive at the optimal threshold levels without needing to calculate the NHB for many combinations of Th1 and Th2, (i.e. it is calculated only for a few combinations). There are various optimization techniques known to the skilled person to achieve this goal.

It will be appreciated that constraints on the possible threshold values can be applied where there are more than two intensity levels of treatment. For example, in the case of three intensity levels (i.e. two thresholds), one of the test thresholds should be higher than the other test threshold.

Furthermore, confidence intervals for the derived threshold value can be estimated by defining distributions of the input parameters (e.g., one-year survival for each intensity level). These distributions can be achieved by defining them as known parametric distributions (e.g., beta distribution for probabilities), or by bootstrapping the local (hospital) data set. Monte-Carlo simulations of the cost-effectiveness model can then be employed to obtain a distribution (and corresponding confidence interval) of the net health benefits and the estimated threshold values.

In case no local data is available to describe the relations in the data, predefined functions can be provided to the data processing system (i.e. the relationships in steps 105 and 107 are predefined). These functions can then be replaced (i.e. steps 105 and 107 repeated) by local relationships once sufficient data is available.

As indicated above, the treatment levels available to a patient as well as the outcomes for the patient and the financial cost may vary by hospital or zip code. As a result, the system 2 can determine threshold values that are valid for a particular hospital or area, or alternatively respective threshold values for multiple hospitals and areas (where the database 4 and 6 contains sufficient information).

In some embodiments, general relationships between the test value of interest and clinical outcomes for each treatment program level can be computed (or derived from the literature) and validated prior to execution of the method in FIG. 4, which means steps 105 and 107 in FIG. 4 comprise adapting or calibrating the general relationships to the specific local patient data stored in the patient information database 4 and treatment/intervention database 6. Different regions may come with a different case-mix (e.g., a higher prevalence of the disease, different age/gender distribution, etc.). Calibration accounts for these issues by adjusting the relationships.

It will be appreciated that the information in the patient information database 4 can be updated or added to over time, which means that steps 105-109 can be repeated using the current information in the database 4 on a regular basis to update the threshold values.

Once the threshold(s) or range of values for each treatment level have been derived according to the invention, they can be used to assign patients to the most cost effective treatment level. In particular, a health care professional can compare a patient's test results with the derived threshold value(s) and read-off the appropriate treatment level for the patient. Alternatively, this process can be automated, with the patient or health care professional inputting the test results into a computer (for example the system 2 or a separate computer system) and the computer outputting the suggested treatment level (alternatively the test result can be supplied directly from the laboratory or home equipment to the computer). The suggested treatment level can be reviewed for suitability by the health care professional in view of the patient's other symptoms and general health condition.

An exemplary user interface 200 allowing manual input of the test results into the computer is shown in FIG. 10. This user interface 200 could be provided by system 2 (i.e. user interface 10) or by a separate computer (including a mobile telephone, smart phone or tablet computer). The user interface 200 includes fields for various pieces of patient specific information such as name, age, gender, body mass index (BMI), blood pressure, urea test result and patient-indicated quality of life. The interface 200 also includes a field for the NTproBNP test result to be entered. Once this test result is input, a recommendation for the most cost effective level of treatment is shown on the interface 200. In the illustrated example, the recommended treatment level is 'Motiva Guide', rather than 'Motiva Coach', 'Motiva Monitor' or 'Usual Care'. The graph provided on the interface 200 also shows the annual hospital costs for each level of treatment.

There is therefore provided a system and method for determining threshold values or a range of values for a test used to assess the current condition of the patient, with the threshold values or range of values being set to indicate the most cost effective intensity level of treatment for the patient having a particular test value.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for facilitating computer-assisted determination of test result thresholds to assign a patient to a particular level of treatment for a clinical condition, the system comprising:
    one or more hardware processors programmed with computer program instructions which, when executed, cause the one or more hardware processors to:
        obtain a request for a recommended treatment level for a patient having a clinical condition, the recommended treatment level request including test result values associated with the patient;
        obtain historical information associated with patients having the clinical condition, the historical information including (i) test result values associated with the patients, (ii) information on treatment levels provided to the patients for the clinical condition, (iii) information on health outcomes of the patients with regard to the clinical condition, the health outcome being measured in terms of one or both of mortality rate or perceived quality of life, and (iv) information on costs associated with providing each of the treatment levels to the patients;
        determine a number of available treatment levels for the clinical condition based on the historical information, the number of available treatment levels specifying how many levels of treatment for the clinical condition are available to be assigned to a given patient;
        determine one or more result value thresholds to be used for assigning a given patient to a particular level of treatment for the clinical condition by:
            responsive to the determined number of available treatment levels being a first number of treatment levels, define a first set of differential equations for determining the one or more result value thresholds, the first set of differential equations configured to assess net health benefits for a first number of candidate sets of result value thresholds to determine the one or more result value thresholds;
            responsive to the determined number of available treatment levels being a second number of treatment levels greater than the first number of treatment levels, (i) define a second set of differential equations and (ii) solve the second set of differential equations via a Levenberg-Marquardt algorithm for determining the one or more result value thresholds, the second set of differential equations configured to assess net health benefits for a second number of candidate sets of result value thresholds to determine the one or more result value thresholds, the second number of candidate sets of result value thresholds being different from the first number of candidate sets of result value thresholds, a number of differential equations in the first set of differential equations being different from a number of differential equations in the second set of differential equations; and
            use the selected set of differential equations to determine the one or more result value thresholds; and
        generate the recommended treatment level for the patient based on the test result values associated with the patient and the one or more result value thresholds.

2. The system as claimed in claim 1, wherein, responsive to the determined number of available treatment levels being the first number of treatment levels, determining the one or more result value thresholds comprises:
    determining, using a linear regression or a logistic regression, a first relationship between the test result values and the information on health outcomes of the patients with regard to the clinical condition;
    determining, using a linear regression or a logistic regression, a second relationship between the test result values and the information on costs associated with providing each of the treatment levels to the patients;
    determining a third relationship between one or more net health benefits and the one or more result value thresholds based on the first relationship and the second relationship, the one or more net health benefits including an accumulated effect of a given treatment level over a given time span measured in quality adjusted life years from which total accumulated costs divided by a willingness-to-pay are subtracted; and
    determining the one or more result value thresholds which results in maximum net health benefits based on the third relationship.

3. The system as claimed in claim 2, wherein the generation of the recommended treatment level for the patient based on the test result values associated with the patient and the one or more result value thresholds further comprises causing the one or more hardware processors to:

compare the test result values to the determined one or more result value thresholds; and generate the recommended treatment level for the patient based on a result of the comparison.

4. The system as claimed in claim 2, wherein the one or more hardware processors are further caused to determine the one or more result value thresholds for respective groups of patients, wherein the respective groups of patients differ from each other in one or more of age, gender, clinical condition, hospital, and geographical area.

5. The system as claimed in claim 2, wherein the willingness-to-pay is a monetary equivalent to a quality-adjusted life year.

6. The system as claimed in claim 1, wherein the determination of the one or more result value thresholds further comprises causing the one or more hardware processors to determine, based on the historical information, a relationship between test result values and a number of patients having test result values at or below the one or more result value thresholds.

7. A method of facilitating computer-assisted determination of test result thresholds to assign patients to a particular level of treatment for a clinical condition, the method comprising:

obtaining, by one or more hardware processors, a request for a recommended treatment level for a patient having a clinical condition, the recommended treatment level request including test result values associated with the patient;

obtaining, by the one or more hardware processors, historical information associated with patients having the clinical condition, the historical information including (i) test result values associated with the patients, (ii) information on treatment levels provided to the patients for the clinical condition, (iii) information on health outcomes of the patients with regard to the clinical condition, the health outcome being measured in terms of one or both of mortality rate or perceived quality of life, and (iv) information on costs associated with providing each of the treatment levels to the patients;

determining, by the one or more hardware processors, a number of available treatment levels for the clinical condition based on the historical information, the number of available treatment levels specifying how many levels of treatment for the clinical condition are available to be assigned to a given patient;

determining, by the one or more hardware processors, one or more result value thresholds to be used for assigning a given patient to a particular level of treatment for the clinical condition by:

responsive to the determined number of available treatment levels being a first number of treatment levels, defining a first set of differential equations for determining the one or more result value thresholds, the first set of differential equations configured to assess net health benefits for a first number of candidate sets of result value thresholds to determine the one or more result value thresholds;

responsive to the determined number of available treatment levels being a second number of treatment levels greater than the first number of treatment levels, (i) defining a second set of differential equations and (ii) solving the second set of differential equations via a Levenberg-Marquardt algorithm for determining the one or more result value thresholds, the second set of differential equations configured to assess net health benefits for a second number of candidate sets of result value thresholds to determine the one or more result value thresholds, the second number of candidate sets of result value thresholds being different from the first number of candidate sets of result value thresholds, a number of differential equations in the first set of differential equations being different from a number of differential equations in the second set of differential equations; and using the selected set of differential equations to determine the one or more result value thresholds; and generating, by the one or more hardware processors, the recommended treatment level for the patient based on the test result values associated with the patient and the one or more result value thresholds.

8. The method as claimed in claim 7, wherein, responsive to the determined number of available treatment levels being the first number of treatment levels, determining the one or more result value thresholds comprises:

determining, using a linear regression or a logistic regression, a first relationship between the test result values and the information on health outcomes of the patients with regard to the clinical condition;

determining, using a linear regression or a logistic regression, a second relationship between the test result values and the information on costs associated with providing each of the treatment levels to the patients;

determining a third relationship between one or more net health benefits and the one or more result value thresholds based on the first relationship and the second relationship, the one or more net health benefits including an accumulated effect of a given treatment level over a given time span measured in quality adjusted life years from which total accumulated costs divided by a willingness-to-pay are subtracted; and determining the one or more result value thresholds which results in maximum net health benefits based on the third relationship.

9. The method as claimed in claim 7, wherein the generation of the recommended treatment level for the patient based on the test result values associated with the patient and the one or more result value thresholds further comprises:

comparing the test result values to the determined one or more result value thresholds; and generating the recommended treatment level for the patient based on a result of the comparison.

10. The method as claimed in claim 8, wherein the willingness-to-pay is a monetary equivalent to a quality-adjusted life year.

* * * * *